(12) United States Patent
Drummond et al.

(10) Patent No.: US 7,216,555 B2
(45) Date of Patent: May 15, 2007

(54) SYSTEM AND METHOD FOR MOBILE SOIL SAMPLING

(75) Inventors: Paul Drummond, Minneapolis, KS (US); Eric Lund, Salina, KS (US); Kevin Collings, Salina, KS (US); Colin Christy, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 245 days.

(21) Appl. No.: 11/056,807

(22) Filed: Feb. 10, 2005

(65) Prior Publication Data

US 2005/0172733 A1 Aug. 11, 2005

Related U.S. Application Data

(60) Provisional application No. 60/544,139, filed on Feb. 11, 2004.

(51) Int. Cl.
*G01N 1/00* (2006.01)
(52) U.S. Cl. .................................. 73/864.45
(58) Field of Classification Search ............ 73/864.81, 73/864.41, 864.42, 864.43, 864.44, 864.45, 73/865.8; 83/919; 175/20, 46, 40
See application file for complete search history.

(56) References Cited

U.S. PATENT DOCUMENTS

| 4,356,734 A | * | 11/1982 | Ivancsics ................. 73/864.31 |
| 5,474,141 A | * | 12/1995 | Hart ............................ 175/20 |
| 6,356,830 B1 | | 3/2002 | Adamchuck et al. |

* cited by examiner

*Primary Examiner*—Robert Raevis
(74) *Attorney, Agent, or Firm*—Jeffrey L. Thompson; Thompson & Thompson, P.A.

(57) ABSTRACT

A soil sampling implement and method have a sampler assembly supported from an implement frame for movement across a field. The sampler assembly includes a tapered cylindrical cutting shoe and a soil collection trough. The cutting shoe has a leading cutting edge arranged for movement through soil in a horizontal direction to cut a cylindrical core sample. A sensing device is provided for measuring at least one soil property. The sampler assembly is moved between a lowered position in which the cutting shoe is positioned at a selected sampling depth, and a raised position in which the cutting shoe is positioned above the soil surface and a soil sample contained in the soil collection trough is brought into contact with the sensing device. A cutting shoe scraper engages and cleans the leading cutting edge of the cutting shoe when the sampler assembly is moved between the lowered and raised positions.

28 Claims, 6 Drawing Sheets

SYSTEM AND METHOD FOR MOBILE SOIL SAMPLING

RELATED APPLICATIONS

This application claims priority of U.S. Provisional Application No. 60/544,139 filed on Feb. 11, 2004.

FIELD OF THE INVENTION

The present invention relates generally to methods and devices for analyzing and mapping soil properties within a field. In particular, the present invention relates to methods and devices for conducting on-the-go soil sampling operations.

BACKGROUND OF THE INVENTION

Accurately and affordably mapping soil properties within a field has proven challenging for precision agriculture practitioners. The sampling density needed to capture small spatial scale variability is impractical using conventional sampling and analysis methods. Those methods involve the insertion of a soil probe into the soil, retracting the probe, removing the soil from the probe, placing the soil into a bag, repeating the process until the bag contains typically 5 to 10 cores, labeling the bag, and sending the composited cores to a soil testing laboratory where the soil is removed, ground, dried, and analyzed.

One of the main hindrances in analyzing soil on-the-go is that most analysis technology requires a certain length of time for an analysis to be completed. Movement of sensors across or through the soil means that sensors do not have the requisite time to measure the soil property of interest. Durability of the analysis equipment is another problem. Abrasion and damage from rocks and other field debris could cause significant damage to most lab sensors. If the soil sample can be extracted on-the-go, and immobilized for measurement, the problems of time and durability are both significantly reduced.

Automated soil collection devices have been developed that collect samples for submission to a soil testing laboratory. These devices provide advantages over the time-consuming and laborious practice of conventional core sampling described above. However, sending a large number of collected samples to a soil testing laboratory to map a field with a desired sampling density is expensive and often impractical.

U.S. Pat. No. 6,356,830 issued to Adamchuk et al. describes a soil collection system having a tray or platform that is dipped into the soil to collect a soil sample and then raised to bring the collected soil into contact with a pH probe. The '830 patent also includes provisions for geo-referencing the pH data. The present invention has been developed as an improvement to the soil sampling system described in the '830 patent and to satisfy a need in the industry for an improved on-the-go soil collection system that overcomes the problems of the prior art.

SUMMARY OF THE INVENTION

An object of the present invention is to provide an improved soil sampling system and method that overcome the problems and shortcomings of the prior art.

A further object of the present invention is to provide an improved soil sampling system that automatically collects and measures properties of a soil sample at predetermined intervals as an implement traverses a field.

A further object of the present invention is to provide a soil sampling system and method that use a soil collection device operating in a horizontal fashion in the soil.

A further object of the present invention is to provide a soil sampling system and method that use a cleaner/scraper to clean soil and plant residue from a previous sample from the leading edge of the soil collection device to improve the reliability of the sample collection.

A further object of the present invention is to provide a soil sampling system having a firming structure for compacting soil ahead of a soil collection device, a row clearing structure for clearing residue ahead of the firming structure, and a closing structure for returning displaced material behind the soil collection device.

A further object of the present invention is to provide a soil sampling system and method that provide automatic cleaning during each cycle of the cutting shoe, safety functions, and various data monitoring/warning features.

A further object of the present invention is to provide a sensor holder with a structure at one end for holding loose soil in contact with an exposed sensor end during a sampling operation.

In order to accomplish these and other objects of the invention, a soil sampling implement and method are provided in which a sampler assembly is supported from an implement frame for movement across a field. The sampler assembly includes a tapered cylindrical cutting shoe and a soil collection trough. The cutting shoe in one embodiment has a leading cutting edge arranged for movement through soil in a horizontal direction to cut a generally cylindrical soil sample. A sensing device is provided for measuring at least one soil property of the core sample. The sampler assembly is moved between a lowered position in which the cutting shoe is positioned at a selected sampling depth beneath the soil surface, and a raised position in which the cutting shoe is positioned above the soil surface and in which a soil sample contained in the soil collection trough is brought into contact with the sensing device. A cutting shoe scraper is arranged to engage and clean the leading cutting edge of the cutting shoe when the sampler assembly is moved between the lowered and raised positions. A firming wheel is arranged to roll over a surface of the soil ahead of the cutting shoe, row cleaners are arranged to clear residue ahead of the firming wheel, and closing disks are arranged to return displaced soil material behind the soil collection trough. A data collection system automatically collects data from the sensing device and location data from GPS indicating the sample locations.

Numerous other objects and features of the present invention will be apparent to those skilled in this art from the following description wherein there is shown and described embodiments of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

A soil sampling implement 10 and method according to the present invention will now be explained with reference to FIGS. 1 to 14 of the drawings. The implement 10 includes a sampler assembly 11 supported from an implement frame 12 for movement across a field to be sampled. The implement frame 12 can be a pull-type frame having gauge/transport wheels 13, tool bars 14, 15, 16, and a tongue 17 for connecting to a prime mover, such as a farm tractor 18. Alternatively, the implement frame can be a three-point mounted frame (not shown) for connecting to a corresponding three-point hitch structure on a tractor, or the implement frame can be self-propelled.

The sampler assembly 11 is mounted to the tool bar 15 of the implement frame 12 via an upper pair of links 19 and a lower pair of links 20. The upper and lower links 19, 20 together form a parallel linkage for supporting the sampler assembly 11. The rear ends 21, 22 of the upper and lower links 19, 20 are pivotally connected to right and left vertical links 23, 24, and the right and left vertical links 23, 24 are connected by upper and lower cross members 25, 26. A channel member 27 is secured to the rear sides of the upper and lower cross members 25, 26. A shank 28 is received in the channel member 27 and secured therein by pins or bolts. Multiple holes 28h are provided in either the shank 28 or the channel member 27 to provide a vertical adjustment of the shank 28 relative to the channel member 27. A handle 29 is provided near the upper end of the shank 28 to facilitate installation and removal of the shank 28.

A hydraulic cylinder 30 is provided for moving the links 19, 20 of the parallel linkage about pivot axes at their forward ends to thereby raise and lower the rear ends 21, 22 of the links 19, 20. The lower end 31 of the hydraulic cylinder 30 is attached to a scraper shank 32 or other stationary portion of the implement frame 12, and the upper end 33 of the hydraulic cylinder 30 is attached to a cross member 34 extending between the upper links 19. The hydraulic cylinder 30 is operable to selectively move the sampler assembly 11 between raised and lowered positions, as explained below. Various other linkage arrangements and mechanisms can also be used to raise and lower the sampler assembly 11.

The sampler assembly 11 includes a cutting shoe 35 and a soil collection trough 36. The cutting shoe 35 has a leading cutting edge 37 arranged for movement through soil in a generally horizontal direction to cut a soil sample. In one embodiment, the cutting shoe 35 is a tapered cylindrical cutting member that cuts a generally cylindrical core sample as the cutting shoe 35 is moved through the soil. For example, the cutting shoe 35 can have a structure similar to conventional cutting shoes used for vertical soil coring probes, except that the cutting shoe 35 is positioned for substantially horizontal movement through the soil. The longitudinal axis 38 of the cutting shoe 35 can be angled slightly upwardly and rearwardly to facilitate entry of the cutting shoe 35 into the soil when the sampler assembly 11 is lowered. For example, the longitudinal axis 38 of the cutting shoe 35 in one embodiment is angled approximately 5 to 30 degrees from horizontal.

As used herein, the term "cutting shoe" can be any soil engaging device that creates a soil core and has a configuration that lets soil flow therethrough. Although the cutting shoe 35 is a cylindrical cutting member in the embodiment described above, other configurations of the cutting shoe can also be used. For example, cutting shoes having oval-shaped or polygonal-shaped cross sections can be used. In each of these embodiments, the leading cutting edge 37 of the cutting shoe 35 is arranged in a closed geometric shape so that a discrete sample can be collected from a desired sampling depth.

A relief area 39 is positioned behind the leading cutting edge 37 of the cutting shoe 35. The relief area 39 has a larger cross section area than the leading cutting edge 37 to facilitate flow of soil through the cutting shoe 35 and into the collection trough 36. A tapered member 40 having a generally vertical cutting edge 41 is provided above the cutting shoe 35 for slicing through soil between the soil surface and the operating depth of the cutting shoe 35. The tapered member 40 is tapered to either side of the shank 15 to allow the sampler assembly 11 to pass through soil with minimal towing force and surface disturbance.

The collection trough 36 is arranged immediately behind the cutting shoe 35 and has a generally semicylindrical shape with an open top side, and side walls 42 defined by the rear portions of the tapered member 40. The collection trough 36 has an open rear side 43 that allows previously sampled soil to be ejected out of the soil collection trough 36 when newly sampled soil passes through the cutting shoe 35 into the collection trough 36.

Figure 1:
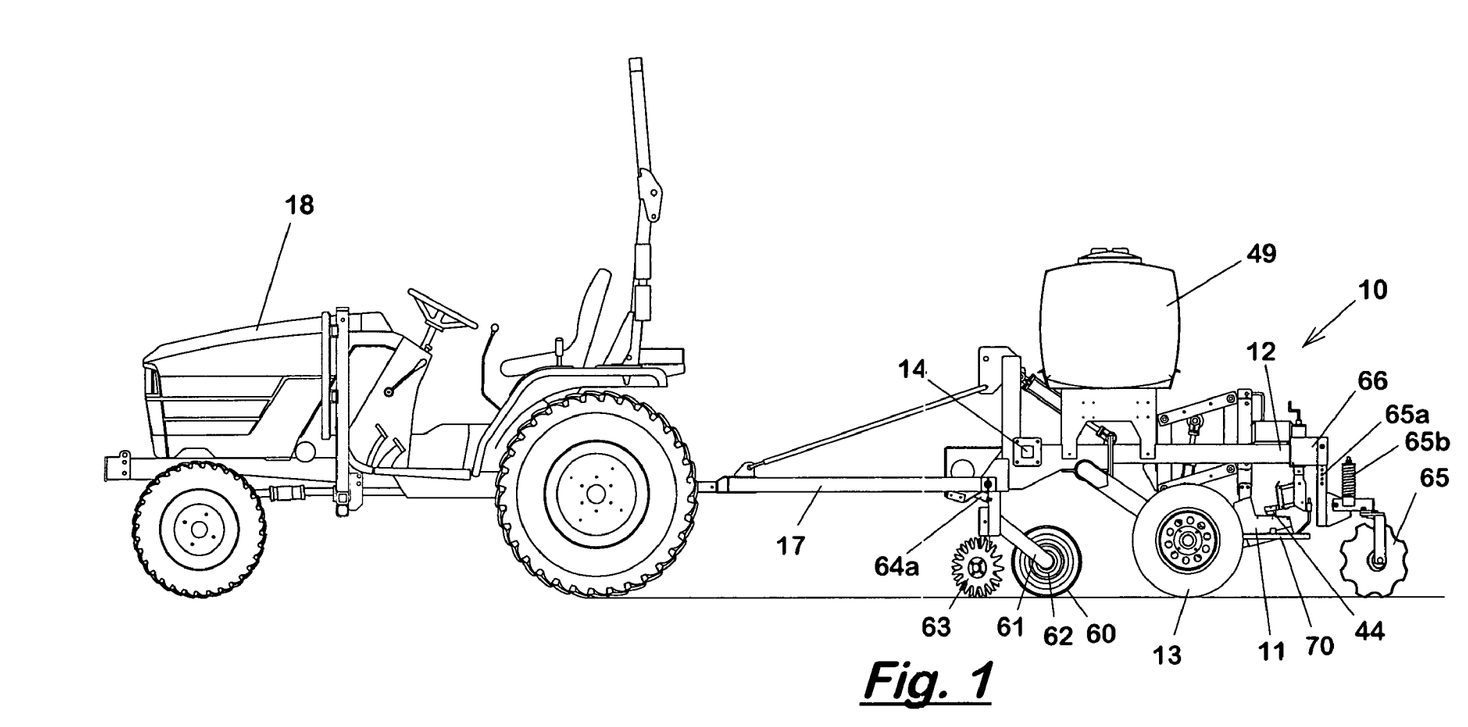
FIG. 1 is a side view of a soil sampling implement of the present invention being towed behind a tractor.
Figure 2:
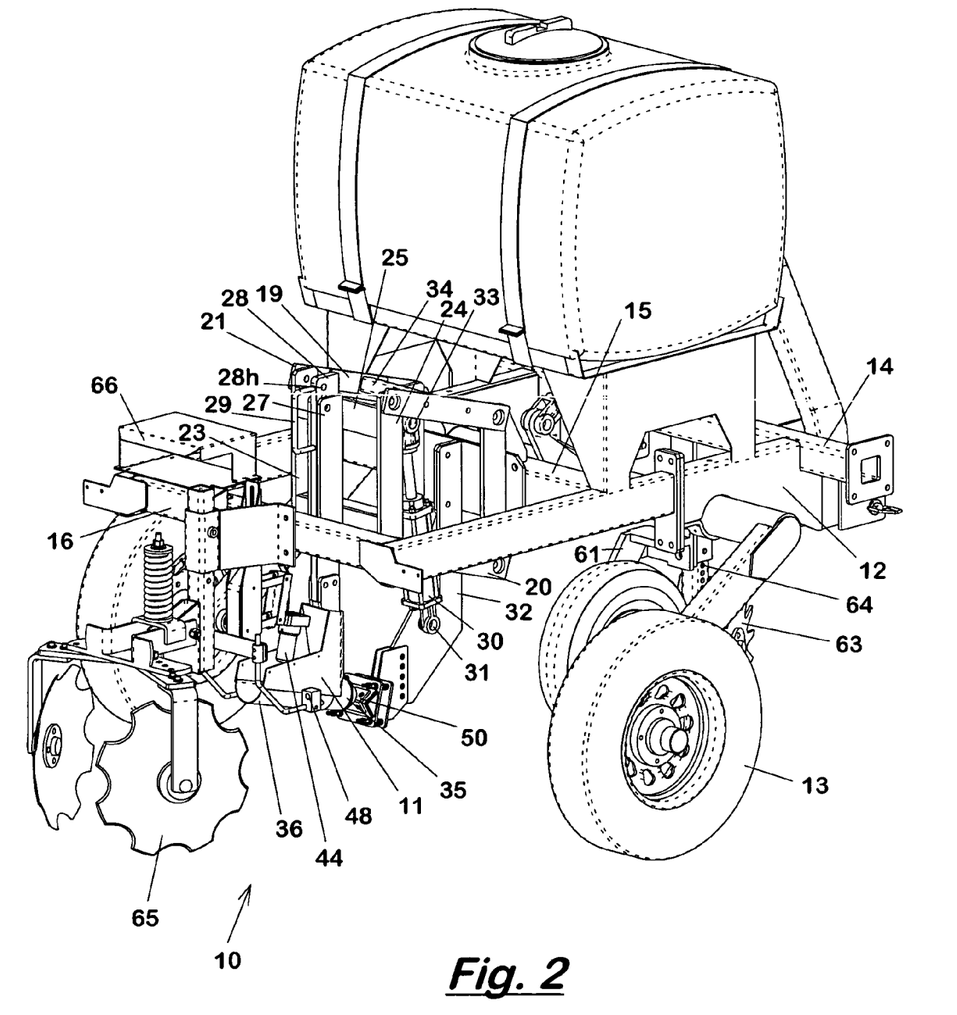
FIG. 2 is a perspective rear view of the soil sampling implement of the present invention.
Figures 3, 4, 5, 6:
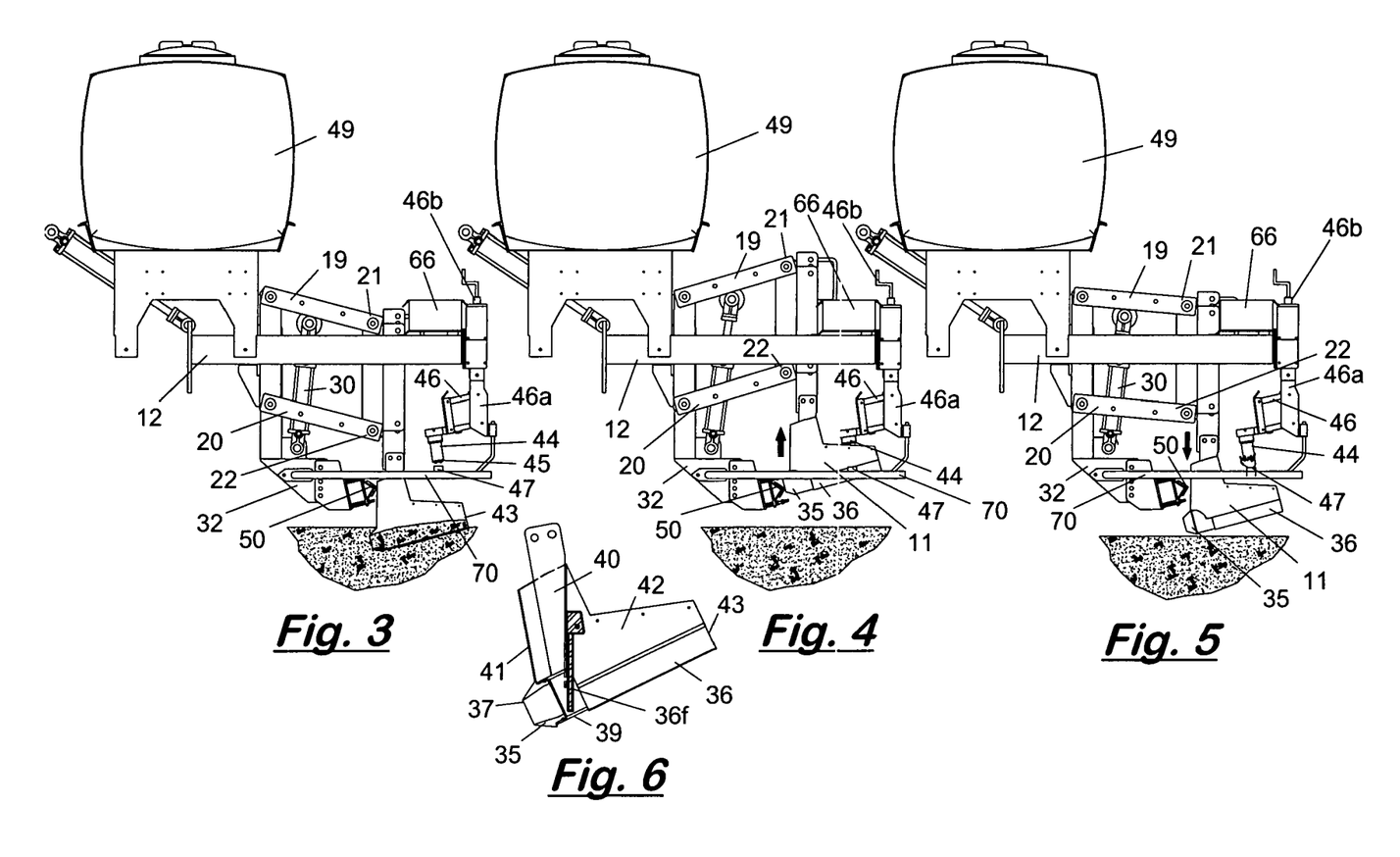
FIG. 3 is a side view showing a lowered position of the sampler assembly of the soil sampling implement of the present invention.
FIG. 4 is a side view similar to FIG. 3 showing an intermediate position of the sampler assembly in which a leading edge of the cutting shoe is engaged by a cutting shoe scraper.
FIG. 5 is a side view similar to FIG. 3 showing another intermediate position of the sampler assembly with a washing system engaged to wash the sensor device as the sampler assembly is being lowered back into the soil to collect another sample.
FIG. 6 is a cross section side view of the sampler assembly showing a sampler shoe flap.

As shown in FIG. 6, a flexible flap 36f is provided between the back of the cutting shoe 35 and the collection trough 36. The flexible flap 36f retards the movement of the soil core through the collection trough 36, particularly at high speeds. The flexible flap 36f can provide an advantage in certain operating conditions, such as where soil core velocity is rapid enough for soil to otherwise flow completely out of the collection trough 36. The flexible flap 36f can be formed, for example, of a rubber material.

A sensing device is mounted above the collection trough 36. The sensing device in one embodiment includes a sensor holder 44 with sensors 45 protruding from or otherwise exposed on a lower end of the sensor holder 44. For example, the sensors 45 can be pH electrodes for sensing soil pH. Alternatively, the sensors 45 can be any suitable sensor or multiple sensors capable of measuring one or more soil properties, such as salinity, water content, organic matter, bulk density, and/or chemical content. Suitable sensors can be provided for sensing any or all of the primary, secondary, and/or trace elements of the soil sample. Various sensing technologies can be employed, including sensors that utilize optical, electromagnetic, electromechanical, and electrochemical technologies to provide in-field measurements.

The soil sample contained in the soil collection trough 36 is brought into contact with the sensors 45 at the lower end of the sensor holder 44 when the sampler assembly 11 is moved to its raised position. The sensor holder 44 is supported by a parallel linkage 46, which is connected to a vertically adjustable shank 46a. A screw jack 46b or other suitable adjustment mechanism connects the shank 46a to the implement frame 12. By adjusting the screw jack 46b, the vertical position of the sensor holder 44 can be changed to fine tune a clearance between the sensors 45 and the trough 36. Such an adjustment may be necessary whenever the operating depth of the cutting shoe 35 is adjusted. The parallel linkage 46 allows the sensor holder 44 to "float" upwardly when the sensors 45 engage the soil in the trough 36. Such floating action allows a uniform pressure to be applied between the sensors 45 and the sampled soil in the trough 36 each time a measurement is taken, accommodates different thicknesses of the soil sample, and protects the sensors 45 from damage.

A washing system is provided to wash the lower end of the sensor holder 44 and the sensors 45 after the sampler assembly 11 is lowered away from the sensor holder 44. The washing system includes right and left nozzles 47, 48 that receive water or other suitable washing fluid under pressure from a storage tank 49 and pump (not shown) carried on the implement 10. The nozzles 47, 48 are ranged to spray water upwardly and inwardly from positions on each side of the sensor holder 44, as depicted in FIG. 5.

Some situations, such as low CEC soils and/or tap water with high total-dissolved solids, require purified wash water. Impurities in tap water, relative to the ionic strength of the soil, can cause the soil pH readings to reflect wash water pH. An onboard reverse-osmosis system with an adequate capacity to handle the flow of wash water can be used to ensure that the soil pH readings are not affected by the wash water pH.

Figures 7, 8, 9:
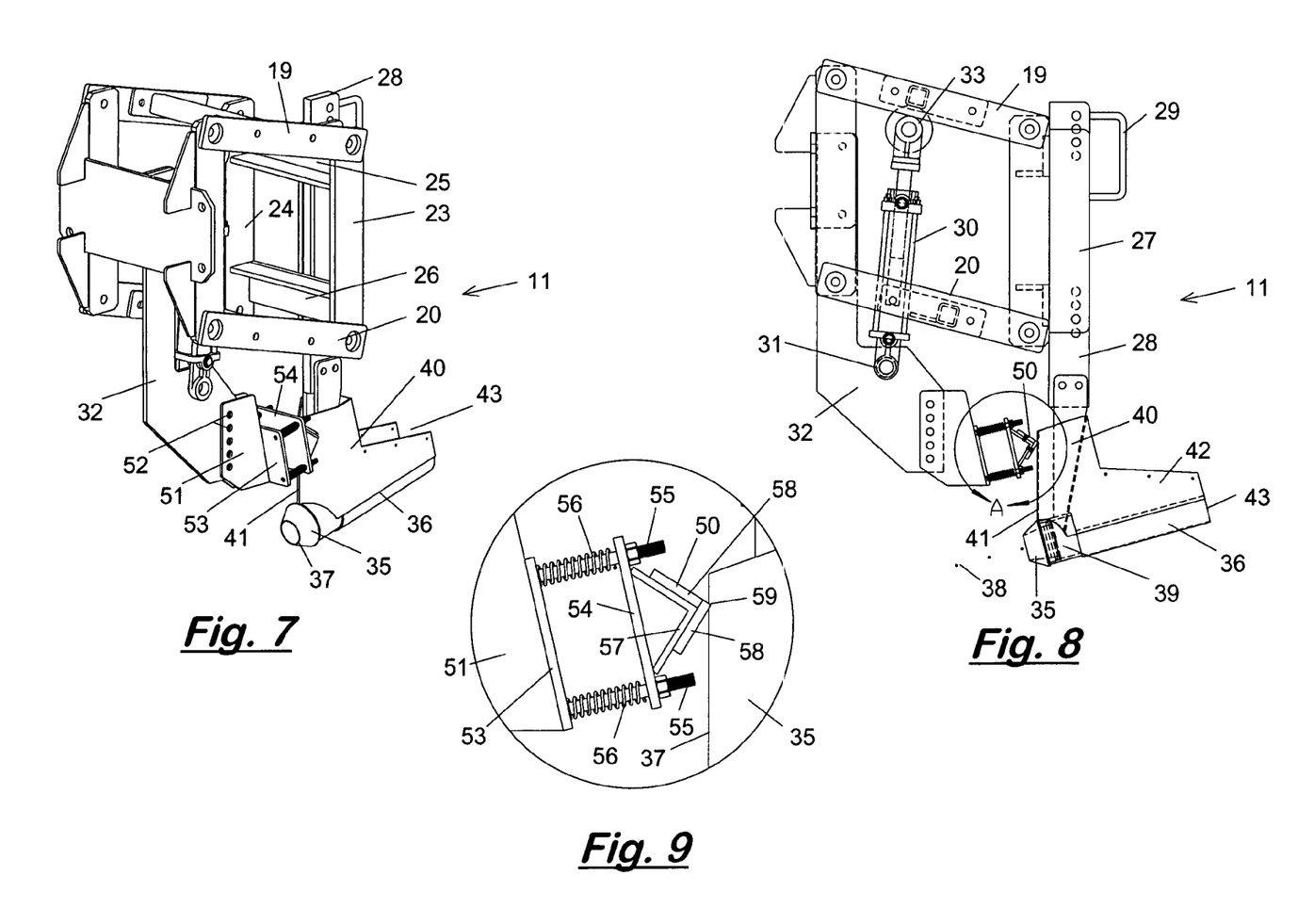
FIG. 7 is a perspective view of the sampler assembly according to the present invention.
FIG. 8 is a side view of the sampler assembly according to the present invention.
FIG. 9 is a detail view showing the cutting shoe scraper engaging the leading edge of the cutting shoe.

A cutting shoe scraper 50 is attached to a lower end of the scraper shank 32 for engaging and cleaning the leading cutting edge 37 of the cutting shoe 35 when the sampler assembly 11 is moved between its lowered and raised positions. The cutting shoe scraper 50 comprises a shank mount structure 51 for attaching to the lower end of the scraper shank 32. The shank mount structure 51 has a plurality of vertically spaced openings 52 that allow the scraper 50 to be attached at a selected vertical position. A first plate 53 is rigidly attached to a rear end of the shank mount structure 51. A second plate 54 is mounted to the first plate 53 using a plurality of bolts 55 and coil springs 56. The coil springs 56 are positioned between the plates 53, 54 with the bolts 55 extending therethrough to allow for resilient movement of the second plate 54 relative to the first plate 53. An angle member 57 is secured to a rear side of the second plate 54, e.g., by welding. A scraper blade 58 is removably attached to the angle member 57, e.g., by threaded bolts or the like. The scraper blade 58 has a generally horizontal cutting edge 59 extending transversely to a direction of travel of the implement 10. The scraper blade 58 can be removed and reconditioned or replaced when the cutting edge 59 becomes too dull or worn to function properly.

The scraper blade 58 of the cutting shoe scraper 50 is positioned in the path of movement of the cutting shoe 35 between its raised and lowered positions. As the cutting shoe 35 is raised, the leading edge 37 of the cutting shoe 35 scrapes across the scraper blade 58 and thereby cleans soil from a previous sample from the leading edge 37. Similarly, as the cutting shoe 35 is lowered, the cutting shoe 35 again scrapes across the scraper blade 58. By cleaning the soil from a previous sample from the leading edge 37 of the cutting shoe 35, the sampler assembly 11 can more reliably collect a new sample because the new soil will flow through with less resistance from the residue of the previous sample contained within the cutting shoe 35.

A firming wheel 60 is provided for rolling over and firming soil ahead of the cutting shoe 35 as the implement 10 traverses a field. The firming wheel 60 is attached to the front tool bar 14 of the implement frame 12 and supported by a suitable arm 61 and hub assembly 62. The firming wheel 60 is used to create the proper soil consistency before passing the cutting shoe 35 through the soil. Other structures for firming the soil ahead of the cutting shoe 35 can be used instead of the firming wheel 60. For example, a firming shank, runner or shoe can be used.

A pair of row cleaners 63 are provided for clearing residue from a surface of the soil ahead of the firming wheel 60. The row cleaners 63 are attached to the front tool bar 14 using a vertical shank 64 that allows adjustment of the vertical position of the row cleaners 63. The row cleaners 63 and the firming wheel 60 can both be supported from a common shank 64 and attached to the tool bar 14 using a parallel linkage 64a or other suitable mounting structure that allows the row cleaners 63 and firming wheel 60 to float relative to the rest of the implement 10. This floating arrangement helps protect the row cleaners 63 against rock damage, and allows the firming wheel 60 to gauge the operating depth of the row cleaners 63 to prevent gouging into the soil.

A pair of closing disks 65 are attached to the tool bar 16 with a vertically adjustable shank 65a at a rear side of the implement frame 12. A compression spring 65b or other suitable structure can be used to control a downward pressure on the closing disks 65, while still allowing the closing disks 65 to float relative to the rest of the implement 10. The closing disks 65 function to return displaced material behind the discharge of the collection trough 36 to minimize soil disturbance.

A stalk guard 70 is attached on each side of the scraper shank 32 and extends outwardly and rearwardly from the scraper shank 32. The stalk guard 70 operates to keep corn stalks and other residue from contacting the wash nozzles 47, sensors 45, and other components of the implement 10. The stalk guard 70 helps prevent damage to the components of the implement 10 and interference with the sampling operations.

Figure 10:
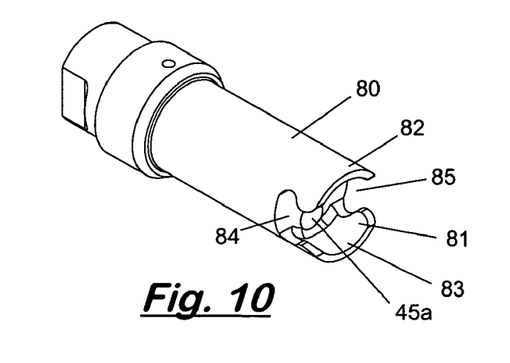
FIG. 10 is a perspective view of a sensor holder having a sand trapper according to a first embodiment.
Figure 11:
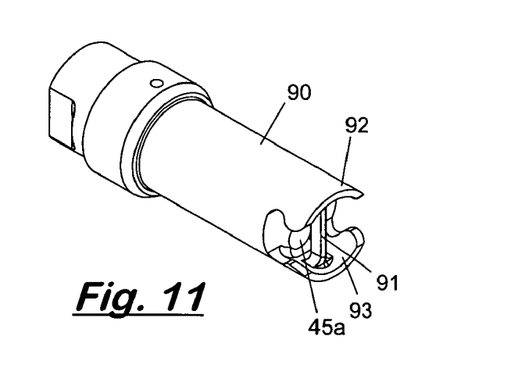
FIG. 11 is a perspective view of a sensor holder having a sand trapper and a soil guard according to a second embodiment.

Modified sensor holders 80 and 90 are shown in FIGS. 10 and 11, respectively. The sensor holders 80, 90 can be used in place of the sensor holder 44 described above to improve performance of the sampling operations in certain soil types. The sensor holders 80, 90 each have a body portion 80a, 90a with at least one longitudinal bore 45a extending therethrough for receiving a sensor 45. In the illustrated embodiments, two bores 45a are provided for receiving a pair of sensors 45. The sensors 45 each have lower ends that protrude from or are otherwise exposed at the lower ends of the bores 45a.

The sensor holder 80 shown in FIG. 10 has a soil trap 81 on its lower end to improve sampling operations, for example, in loose sandy soil. The soil trap 81 has a generally cylindrical configuration with front and rear wall portions 82, 83 and cut-away openings 84, 85 on each side. The front and rear wall portions 82, 83 create a trap for holding loose soil, such as sandy soil, in contact with the exposed lower ends of the sensors 45. The cut-away side openings 84, 85 allow wash water from the nozzles 47 to pass into the soil trap 81 from each side to wash away any soil remaining in the soil trap 81 after the soil trough 36 is lowered away from the sensor holder 80.

Figure 12:
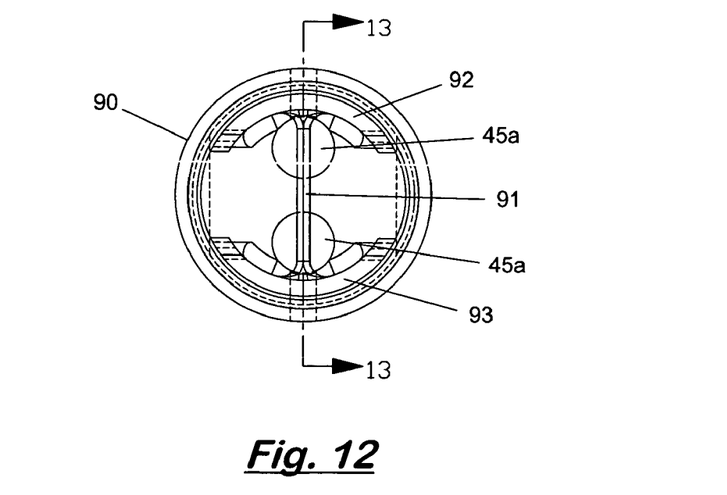
FIG. 12 is a bottom end view of the sensor holder shown in FIG. 11.
Figure 13:
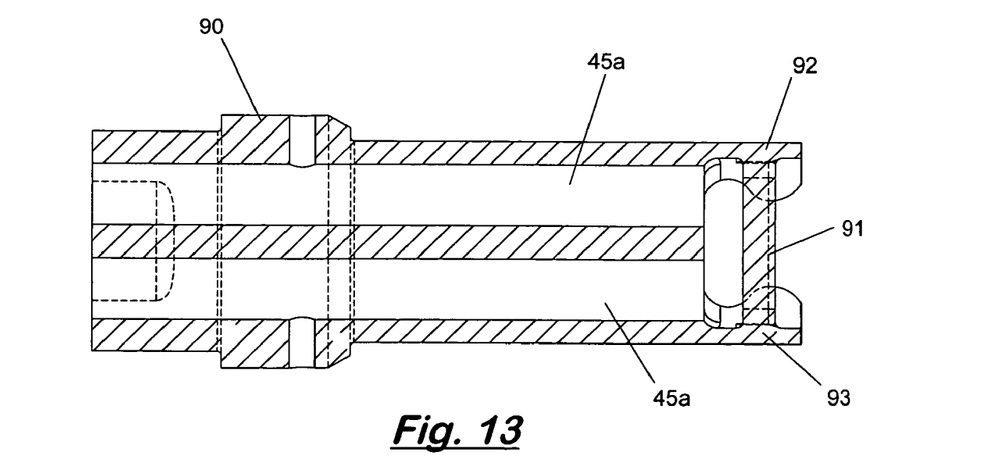
FIG. 13 is a cross section side view of the sensor holder shown in FIG. 11, as viewed along the line 13—13 in FIG. 12.

The sensor holder 90 shown in FIGS. 11 to 13 is structurally the same as the sensor holder 80 shown in FIG. 10, except that the sensor holder 90 includes a soil guard 91 extending between the front and rear wall portions 92, 93. The soil guard 91 allows soil to flow into contact with the sensors 45, but protects the sensitive lower ends of the sensors 45 from a direct push against the soil, and particularly the abrasive particles within the soil. As a result, the soil guard 91 reduces abrasion on the exposed tips of the sensors 45.

A suitable monitoring device (not shown) can be provided to monitor the flow of soil through the cutting shoe 35 and to warn of any plugging. The monitoring device can be an electronic and/or mechanical sensor that detects whether the soil within the cutting shoe 35 is moving and outputs a warning signal to the control system when plugging is detected.

An onboard computer 66 provides the control system for controlling the implement 10 to automatically collect and measure soil samples. The operation of the soil sampling implement 10 and the control system will now be explained with reference to the flow chart shown in FIG. 14 of the drawings.

Figure 14:
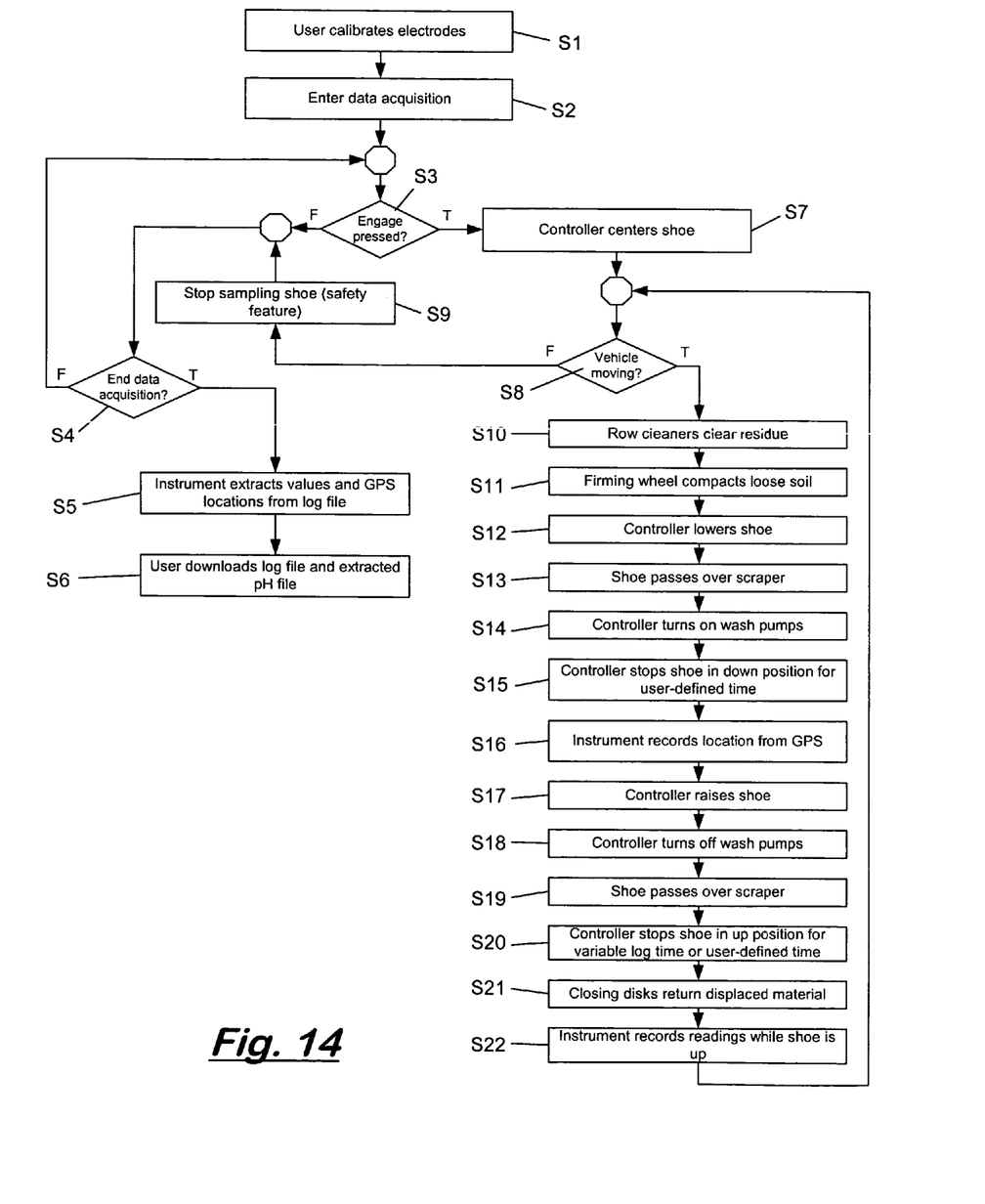
FIG. 14 is a flow chart of the soil sampling method according to the present invention.

The operation starts by having the user calibrate the electrodes or other sensors 45 in step S1, and then entering a data acquisition mode in step S2. A determination is then made in step S3 whether the user has engaged a switch to start the sampling. If not, the control continues in the data acquisition mode until a determination is made in step S4 to end data acquisition. When the data acquisition mode is ended, the instrument extracts values and GPS locations from a log file in step S5, and the user downloads the log file and extracted pH (or other measured soil parameter) file in step S6.

During the data acquisition mode, the control returns to step S3 until the user engages the system to start sampling operations. At this point, the control moves to step S7 and the controller centers the cutting shoe 35 at an intermediate position between its raised and lowered positions. The control then determines in step S8 whether the vehicle is moving. If the vehicle is not moving, the control goes to step S9 and the cutting shoe 35 is prevented from being lowered as a safety feature. Once the vehicle begins moving, the control goes to step S10 and continues to cycle through steps S10 to S22 until the vehicle is stopped again.

As the soil sampling implement 10 is moved through the field, the row cleaners 63 clear residue ahead of the firming wheel 60 in step S10, and the firming wheel 60 compacts loose soil ahead of the cutting shoe 35 in step S11. The controller then lowers the cutting shoe 35 in step S12, and the cutting shoe 35 passes over the scraper 50 in step S13. The controller then turns on the wash pump in step S14 to spray water from the nozzles 47, 48 onto the sensing device 44. The controller keeps the cutting shoe 35 in its lowered position for a user-defined time in step S15 during which time the firmed soil at the desired sampling depth flows through the cutting shoe 35 and exits the rear of the collection trough 36.

The instrument records a location from GPS into the log file in step S16, and the controller raises the cutting shoe 35 in step S17. The controller then turns off the wash pump in step S18, and the cutting shoe 35 passes over the scraper 50 in step S19 as it moves to its raised position. In step S20, the controller stops the cutting shoe 35 in its raised position with the collected soil sample in contact with the sensors 45 for a variable time based on a programmable criteria (e.g., settling time or user-defined time). In one embodiment, the programmable criteria relates to a settling of the pH measurement. For example, the programmable criteria can require four successive pH readings that are within 0.02 pH of each other, along with a minimum and maximum reading time (e.g., 7 to 25 seconds). Such programmable criteria can maximize cycling frequency while generating high quality data. The measurement stability can also be improved by averaging multiple measurements for each soil sample. A visible or audible warning can be provided in the event the log time goes over a predetermined time (e.g., 10 seconds), allowing the operator to slow down to avoid large gaps in the field being measured. If the condition persists, the operator can then check the sensors 45 or sampling mechanism for problems.

The closing disks 65 return displaced material behind the collection trough 36 in step S21. After the settling time or user-defined time passes in step S20, the instrument records the readings from the sensors 45 in step 522 while the cutting shoe 35 remains in its raised position. The operation then cycles back to step S10 and additional samples are collected and measured as the implement 10 continues to move across the field.

In practice, the operator of the present invention initiates an automatic cycling sequence and drives the towing vehicle forward. The sampler assembly 11 then lowers into the soil, and the cutting shoe 35 creates a soil core that flows into and through the collection trough 36. This action forces the previous soil sample out the rear of the collection trough 36. Within a short time (e.g., 2 to 5 seconds) after entering the soil, the hydraulic cylinder 30 raises the collection trough 36 containing the soil core out of the soil, bringing the new soil core into contact with the sensors 45.

During each raising and lowering cycle the leading edge 37 of the cutting shoe 35 is cleaned by the cutting shoe scraper 50. This cleaning enhances the operation of the system. In loose soil conditions, firming the soil ahead of the sampler assembly 11 can improve the operation by causing the soil to flow more consistently into the cutting shoe 35 and through the sampler collection trough 36. The firming wheel 60 accomplishes this by creating a firmed track in the soil ahead of the cutting shoe 35.

As described above, the present invention provides an on-the-go soil sampling system that automatically collects soil samples and presents the samples to various sensing devices for measurement, and discharges the sample as it acquires the next sample. The data collected from the sensing devices are recorded, along with the geo-referenced position of the sample location, on a data collection/monitoring instrument. The entire process is automated; after initiating the process, the vehicle operator merely drives the towing vehicle and monitors the sampling process via the data collection/monitoring instrument. With this system, 5 to 10 times as many samples can be taken compared to conventional sampling techniques, resulting in a significantly more accurate representation of the soil variability within the field.

It will be appreciated that certain features of the present invention described above can be changed without departing from the scope of the invention. For example, a cutting trough can be used in place of the cutting shoe 35 described above. A cutting trough may not provide the same advantages of a cutting shoe having a leading cutting edge with a closed geometric shape, particularly a round shape as disclosed herein, but could still provide a viable working embodiment if used in conjunction with a scraper assembly and/or other features of the present invention.

While the invention has been specifically described in connection with specific embodiments thereof, it is to be understood that this is by way of illustration and not of limitation, and the scope of the appended claims should be construed as broadly as the prior art will permit.

What is claimed is:

1. A method of sampling soil, comprising the steps of:
providing a cutting shoe having a soil cutting edge arranged in a closed geometric shape, and a soil collection trough positioned behind the cutting shoe;
moving the cutting shoe and soil collection trough through soil substantially horizontally with the closed geometric shape of the in cutting edge at a controlled depth beneath the soil surface to collect a first soil core sample from a desired sampling depth;
raising the cutting shoe and soil collection trough out of the soil;
moving the first soil sample contained in the soil collection trough into contact with a sensor for measuring a property of the soil;
lowering the cutting shoe and soil collection trough back into the soil; and
moving the cutting shoe and soil collection trough through the soil substantially horizontally to collect a second soil sample while causing the first soil sample to be ejected out of the sampler trough.

2. The method of sampling soil according to claim 1, wherein said cutting shoe and soil collection trough are mounted on an implement, and wherein said implement is moved continuously across a field while a plurality of samples are collected from the field.

3. The method of sampling soil according to claim 1, further comprising the step of scraping a leading edge of the cutting shoe to clean soil from a previous sample from the leading edge before lowering the cutting shoe back into the soil to collect a new sample.

4. The method of sampling soil according to claim 1, wherein said cutting shoe comprises an oval-shaped cross section.

5. The method of sampling soil according to claim 1, wherein said cutting shoe comprises a cylindrical cutting member that cuts a cylindrical core sample.

6. The method of sampling soil according to claim 1, wherein said cutting shoe and soil collection trough are mounted on an implement, and further comprising the step of using a soil firming device mounted on said implement to firm soil ahead of the cutting shoe.

7. The method of sampling soil according to claim 6, further comprising the step of using a residue clearing device mounted on said implement to clear residue from a surface of the soil before firming the soil.

8. The method of sampling soil according to claim 1, further comprising the step of washing the sensor between each sample.

9. The method of sampling soil according to claim 1, further comprising the step of measuring a pH of the soil when the soil samples are moved into contact with the sensor.

10. The method of sampling soil according to claim 1, further comprising the step of measuring a soil sample property selected from the group consisting of salinity, water content, organic matter, bulk density, and chemical content of the soil, when the soil samples are moved into contact with the sensor.

11. The method of sampling soil according to claim 1, wherein said cutting shoe and soil collection trough are mounted on an implement, which is moved continuously across a field while a plurality of samples are collected from the field and moved into contact with the sensor, and further comprising the step of recording measurement data from the sensor together with geo-referenced position data corresponding to the sample location.

12. A method of sampling soil, comprising the steps of:
moving a cutting shoe and soil collection trough through soil substantially horizontally at a controlled depth to collect a first soil sample;
raising the cutting shoe and soil collection trough out of the soil;
moving the first soil sample into contact with a sensor for measuring a property of the soil;
lowering the cutting shoe and soil collection trough back into the soil; and
moving the cutting shoe and soil collection trough through the soil substantially horizontally to collect a second soil sample while causing the first soil sample to be ejected out the rear of the sampler trough;
wherein said cutting shoe comprises a tapered cylindrical cutting member that cuts a cylindrical core sample as the cutting shoe is moved substantially horizontally through the soil.

13. A soil sampling implement, comprising:
a sampler assembly supported from an implement frame, said sampler assembly including a cutting shoe and a soil collection trough positioned behind said cutting shoe, said cutting shoe having a soil cutting edge arranged in a closed geometric shape for movement through soil in a substantially horizontal direction to cut a soil core sample;
a sensing device for measuring at least one soil property; and
a means for moving the sampler assembly between a lowered position in which the closed geometric shape of the soil cutting edge of the cutting shoe is positioned at a selected sampling depth beneath the soil surface, and a raised position in which the cutting shoe is positioned above the soil surface and in which a soil core sample contained in the soil collection trough is brought into contact with the sensing device.

14. The soil sampling implement according to claim 13, further comprising a cutting shoe scraper arranged to engage and clean the leading cutting edge of the cutting shoe when the sampler assembly is moved between the lowered and raised positions.

15. The soil sampling implement according to claim 13, wherein said cutting shoe further comprises a relief area positioned behind the cutting edge, said relief area having a larger cross section area than a cross section area of the closed geometric shape of said cutting edge.

16. The soil sampling implement according to claim 13, wherein said soil collection trough is arranged immediately behind the cutting shoe so that movement of newly sampled soil through the cutting shoe causes previously sampled soil to be ejected out a rear of the soil collection trough.

17. The soil sampling implement according to claim 16, further comprising a flexible flap positioned between a discharge end of the cutting shoe and the soil collection trough for retarding a flow of soil through the soil collection trough.

18. The soil sampling implement according to claim 13, further comprising a firming device arranged to firm soil ahead of the cutting shoe as the implement traverses a field.

19. The soil sampling implement according to claim 18, further comprising a residue clearing device for clearing residue from a surface of the soil ahead of said firming device.

20. The soil sampling implement according to claim 19, wherein said firming device and said residue clearing device are mounted on a common assembly for floating movement together relative to the implement frame.

21. The soil sampling implement according to claim 13, further comprising a spray wash system for washing the sensing device between each sample.

22. The soil sampling implement according to claim 13, wherein said sensing device comprises pH electrodes for sensing soil pH.

23. The soil sampling implement according to claim 13, wherein said sensing device comprises a sensor for measuring at least one soil sample property selected from the group consisting of salinity, water content, organic matter, bulk density, and chemical content of the soil.

24. The soil sampling implement according to claim 13, further comprising a data acquisition system for recording measurement data from said sensor device together wit geo-referenced position data corresponding to the sample location.

25. The soil sampling implement according to claim 13, wherein said cutting shoe comprises an oval-shaped cross section.

26. The soil sampling implement according to claim 13, wherein said cutting shoe comprises a cylindrical cutting member that cuts a cylindrical core sample.

27. A soil sampling implement, comprising:
a sampler assembly supported from an implement frame, said sampler assembly including a cutting shoe and a soil collection trough said cutting shoe having a leading cutting edge arranged for movement through soil in a substantially horizontal direction to cut a soil sample;
a sensing device for measuring at least one soil property; and
a means for moving the sampler assembly between a lowered position in which the cutting shoe is positioned at a selected sampling depth beneath the soil surface, and a raised position in which the cutting shoe is positioned above the soil surface and in which a soil sample contained in the soil collection trough is brought into contact with the sensing device; comprises a tapered cylindrical cutting member arranged to cut a cylindrical core sample as the cutting shoe is moved through the soil.

28. A soil sampling implement comprising:
a soil sampler assembly supported from an implement frame, said soil sampler assembly including a soil engaging device having a leading cutting edge arranged for movement through soil in a substantially horizontal direction to cut a soil sample;
means for moving the sampler assembly between a lowered position in which the soil engaging device is positioned at a selected sampling depth beneath the soil surface, and a raised position in which the soil engaging device is positioned above the soil surface; and
a scraper arranged to engage and clean the leading cutting edge of the soil engaging device when the sampler assembly is moved between the lowered and raised positions.

* * * * *